US006235948B1

(12) United States Patent
Sunkara et al.

(10) Patent No.: US 6,235,948 B1
(45) Date of Patent: May 22, 2001

(54) PROCESS FOR THE PURIFICATION OF 1,3-PROPANEDIOL

(75) Inventors: Hari Babu Sunkara, Wilmington, DE (US); Robert John Umile, II, Boothwyn, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/374,942

(22) Filed: Aug. 16, 1999

Related U.S. Application Data

(60) Provisional application No. 60/096,939, filed on Aug. 18, 1998.

(51) Int. Cl.[7] .................................................. C07C 29/76
(52) U.S. Cl. ........................................... 568/868; 568/872
(58) Field of Search ...................................... 568/868, 872

(56) References Cited

U.S. PATENT DOCUMENTS

| 2,520,733 | 8/1950 | Morris et al. | 260/615 |
| 3,326,985 | 6/1967 | Mason | 260/615 |
| 4,937,314 | 6/1990 | Greene | 528/272 |
| 4,970,295 | 11/1990 | Schuchardt | 528/416 |
| 5,008,473 | 4/1991 | Breitkopf et al. | 568/868 |
| 5,128,185 | 7/1992 | Greene | 428/36.9 |
| 5,194,159 | 3/1993 | George et al. | 210/654 |
| 5,364,987 | 11/1994 | Haas et al. | 568/866 |
| 5,403,912 | 4/1995 | Gunatillake et al. | 528/425 |
| 5,527,973 | 6/1996 | Kelsey | 568/862 |
| 5,659,089 | 8/1997 | Cai et al. | 568/619 |

OTHER PUBLICATIONS

M. J. Rhoad and P.J. flory, J. Am. Chem. Soc. 72, 2216 (1949).

Nafion® Superacid Resins NR–50 and NR–40 Product Information.

Nafion® SAC Superacid Catalyst Product Information (1999).

*Primary Examiner*—Peter O'Sullivan

(57) ABSTRACT

Disclosed is a process for the removal of impurities, especially color forming impurities, from 1,3-propanediol.

26 Claims, No Drawings

PROCESS FOR THE PURIFICATION OF 1,3-PROPANEDIOL

This application claims the benefit of Provisional No. 60/096,939 filed Aug. 18, 1998.

FIELD OF THE INVENTION

This invention concerns a process for the removal of impurities, especially color forming impurities, from 1,3-propanediol.

TECHNICAL BACKGROUND OF THE INVENTION 1,3-Propanediol is a precursor for polyether glycols, polyester bomopolymers and copolymers, and thermoplastic elastomers. The quality of these products is in general dependent on the quality of the raw materials. For some applications, such as fibers, color quality is a major concern. It is known that products derived from 1,3-propanediol have suffered from discoloration. Commercially available samples of 1,3-propanediol starting materials have resulted in brown colored polyether glycols. Disclosed attempts to remove color from the products made from available 1,3-propanediol have been laborious and expensive. Even after extensive purification processes, many products retain a yellow color.

U.S. Pat. No. 2,520,733 discloses a process for the purification of polyols prepared from 1,3-propanediol in the presence of acid catalyst (2.5 to 6% by weight) and at a temperature from about 175° C. to 200° C. This purification process involves percolation of the polymer through Fuller's earth followed by hydrogenation. Even after this extensive purification process, the final product remains light yellow in color.

U.S. Pat. No. 3,326,985 discloses a procedure for the preparation of poly(1,3-propanediol) of molecular weights in the range of 1200–1400 possessing improved color by vacuum stripping, under nitrogen, poly(1,3-propanediol) of lower molecular weight.

U.S. Pat. No. 5,659,089 discloses a process for the preparation of poly(2-methyl-1,3-propanediol) by the etherification of 2-methyl-1,3-propanediol. No diol purification process is given. Any available grade of diol can be used in the etherification process.

U.S. Pat. No. 5,527,973 discloses a process for providing a purified 1,3 propanediol which can be used as a starting material for low color polyester. That process has several disadvantages including the use of large equipment and the need for dilution with large quantities of water which is difficult to remove from the product.

The process of the present invention alleviates the problem of discolored polymer production in a relatively simple and economical process. The process of the present invention involves purification of, and removal of color precursors from the starting reactant 1,3-propanediol rather than treating the resulting products. The purified diol from this process is useful for preparing a variety of polymers that include polyether glycols, polyesters and thermoplastic elastomers having excellent color characteristics.

SUMMARY OF THE INVENTION

Disclosed is a process for the purification of 1,3-propanediol comprising the steps of a) contacting 1,3-propanediol with an acid catalyst at a temperature above that required for impurities to react and below that required for extensive ether formation; and b) separating purified 1,3-propanediol from impurities, reacted impurities and the acid catalyst.

DETAILED DESCRIPTION OF THE INVENTION

In the preparation of low molecular weight polyether glycols via the dehydration of 1,3-propanediol, polyol quality is an important item. For some applications, such as the production of fibers, color is a major concern. In the past, attempts to prepare polytrimethylene glycols having good color properties have been unsuccessful. This invention discloses a process for the preparation of purified 1,3-propanediol so that products made from it, polyols, polyester homopolymers and copolymers, and thermoplastic elastomers, have excellent color characteristics.

Color-free, i.e., chromophore-free, polyether glycols have been prepared from 1,3-propanediol that has been purified of chromophore precursors by a two step process. The first step in the treatment of the diol to free it of color formers (referred to herein as "color precursors") involves the contacting of the 1,3-propanediol with an acid catalyst at elevated temperatures. While not wishing to be bound by any mechanism, applicant believes this step converts color precursors and other impurities to colored and uncolored derivatives that, due to their changed chemical nature, are easily separable from 1,3-propanediol. The second step of the purification process involves the separation of the desirable, purified 1,3-propanediol from the formed colored and uncolored derivatives, from the acid catalyst employed to effect the conversion and, potentially, from residual impurities.

An acid catalyst is employed in the treatment process. This acid catalyst promotes the conversion of chromophore precursors to chromophores. The type of acid, (homogeneous or heterogeneous), nature (strong or weak) and the amount of acid catalyst can be varied widely. Although soluble acid catalysts, including inorganic acids and organic sulfonic acids, can be used, heterogeneous acid catalysts are usually preferred because they can be removed more easily and can easily be recycled. Soluble catalysts, if used, can be removed by extraction or neutralization. Solid heterogeneous acid catalysts can be removed by filtration. Fixed heterogeneous catalyst may also be used, i.e., in a continuous process, provided that contact time is sufficient. Suitable heterogeneous catalysts are perfluorinated ion-exchange polymers (PFIEP) containing pendant sulfonic acid groups or pendant carboxylic acid groups, including Nafion® catalyst, obtainable from the DuPont Company, which is an example of perfluorinated ion-exchange polymers containing pendant sulfonic acid groups, silica or alumina supported Nafion® catalyst, Nafion® Superacid catalyst, a porous nanocomposite of Nafion® resin and silica, acid zeolites, or acid clays.

The amount of acid catalyst used herein is not critical, as long as sufficient catalyst is present. Small amounts of catalyst may necessitate extended treatment times. In the case of commercial Nafion® NR50 catalyst, 1% by weight of catalyst versus the weight of 1,3-propanediol was convenient in a batch treatment process. The amount of catalyst employed, in batch treatment processes, will generally be within the range of about 0.1 to 5 wt % based on the amount of 1,3-propanediol used.

The temperature for the acid treatment step is selected such that the reaction that converts chromophore precursors readily occurs, but the dehydration reaction of 1,3-propanediol is essentially avoided. The process of the invention is carried out by heating the 1,3-propanediol and the acid catalyst at a temperature within the range of about 100–160° C. for 0.1–3 hours under nitrogen atmosphere. At temperature greater than 170° C., the acid can function as a dehydrating catalyst that could lead to the formation of polyether glycols from the 1,3-propanediol. Preferably, the reaction temperature is maintained within the range of 130° C.–150° C. so that chromophore precursor reaction occurs but essentially no dimers or trimers of 1,3-propanediol are formed.

The acid treatment is most conveniently carried out at atmospheric or above atmospheric pressures.

In a preferred mode of operation, after the color precursors are transformed, the mixture is cooled to room temperature, and the solid catalyst is removed either by filtration or by decantation. The filtered mixture is then distilled under reduced pressure, and the 1,3-propanediol is collected. The colored impurities and other impurities are left in the distillation flask. The absence of acid catalyst during the vacuum distillation process limits the occurrence of 1,3-propanediol dehydration reactions.

The purification of 1,3-propanediol, as described above, can be carried out in either a batch process or a continuous process. The treatment maybe carried out in an agitated system or, if the acid catalyst is in solid form or adhered/attached to a solid support, the treatment may be carried out by passing the diol over or through a bed of the solid acid catalyst.

The process can be conducted as a stand alone process, carried out on available 1,3-propanediol. Alternatively, it may be integrated within a 1,3-propanediol manufacturing process—carried out as one of the steps of a 1,3-propanediol manufacturing process. The 1,3-propanediol may be prepared by a variety of manufacturing processes, including the hydration of acrolein followed by hydrogenation of the resulting hydroxypropanal, or the hydroformylation of ethylene oxide followed by reduction of the resulting hydroxypropanal. The purification process may by integrated within either of these or other manufacturing processes.

The purified 1,3-propanediol is isolated by means known in the art, most preferably by vacuum distilling the diol away from the converted color precursors and colored and uncolored derivatives.

In subsequent processing, the purified diol may be polymerized in the presence of either soluble or insoluble acid catalyst to obtain colorless polyether polyol of low molecular weights. In alternate end uses, the purified diol may be used to prepare polyesters, for example poly(1,3-propylene terephthalate) by methods known in the art.

Depending upon the intensity of the color of the samples to be measured, two different color scales are used. For light colored products, Platinum-Cobalt (APHA) Standard and for dark colored products Gardner Standard are used.

EXAMPLES

Example 1

Purification Process of 1,3-propanediol Using Nafion® Acid Catalyst

A 5 L-three necked flask equipped with a distillation column, mechanical stirrer and nitrogen inlet was charged with 1,3-propanediol (3714.2 g) (commercial grade, Degussa) and Nafion® NR50 catalyst (37.147 g)(DuPont). The mixture was stirred mechanically and heated to 130° C. under nitrogen atmosphere. At this temperature, the liquid turned yellow. The liquid then turned brown as it was heated to 150° C. The temperature was kept constant at 150° C. for about 2 hours and then allowed to cool to room temperature. No distillate was collected at the receiver flask indicating that essentially no dehydration reaction occurred under these conditions. The solid acid catalyst was removed by decanting the colored solution. Then, the diol was isolated from the colored impurities by distilling at 100° C. under reduced pressure. The APHA color values as measured on a HunterLab ColorQuest (Hunter Associates Laboratory, Inc., Reston, Va.) for the purified diol and the original diol are 3 and 7 respectively, indicating an improvement in color characteristics of the purified diol.

Heating the thus purified 1,3-propanediol to reflux, under nitrogen, for 3 hours caused the APHA color to increase from 3 to 20. Similar treatment of the starting 1,3-propanediol gave a colored product having APHA color of 60 (i.e., a change from 7 to 60 APHA color). Example 2, below, and comparative example 1, wherein these two samples of 1,3-propanediol are converted to poly(1,3-propanediol) further illustrate the efficacy of the process of the present invention in removing color forming impurities.

Example 2

Synthesis of Poly(1,3-propanediol) from Purified 1,3-propanediol

To a 250 mL three-necked flask, 152.2 g (2.0 mol) of purified 1,3-propanediol, prepared as in Example 1, and 1.903 g (10 mmol) of p-toluenesulfonic acid (Aldrich Chemical Co, Milwaukee, Wis.) were added at room temperature. The mixture was stirred and heated to 180–200° C. under nitrogen atmosphere. The distillate (33.1 mL), mostly water was collected as the dehydration reaction progress. The reaction was stopped after 5.5 hours and the mixture was cooled to room temperature. Colorless poly(1,3-propanediol) was obtained from this process. The APHA color value for the polyol was measured and had a value of 48.

Comparative Example 1

Synthesis of Poly(1,3-propanediol) from Unpurified 1,3-propanediol

To 152.2 g (2.0 mol) of 1,3-propanediol (commercial grade, Degussa), 1.903 g (10 mmol) of p-toluenesulfonic acid was added. The mixture was stirred and heated under nitrogen atmosphere. As the temperature of the reaction mixture increased, the color formation was observed at the temperature of 130° C. and then the dehydration reaction occurred at 180–200° C. About 32.5 mL of distillate was collected during the dehydration reaction which continued for a time period of 5.5 hours. The color properties of the polyol was measured and had a APHA color value of >300, i.e., off the APHA color scale. The color was measured in Gardner units using a Hellige Daylite Comparator Illuminator (Hellige, Inc., Garden City, N.Y.) which gave a Gardner value of 4.

Example 3

A Larger Scale Diol Purification

The 1,3-propanediol purification process described in Example 1 was scaled up. A 30-gallon glass-lined clave was charged with polymer grade 1,3-propanediol (176 lb) and Nafion® NR50 catalyst (1.76 lb). The mixture was stirred mechanically and heated to 150° C. under nitrogen atmosphere. The temperature was kept constant at 150° C. for about two hours and then allowed to cool to room temperature. After cooling, the clave was discharged through a filter to recover the solid acid catalyst. The discolored diol solution, that has an APHA color value greater than 300, was distilled in batches using a 22 L-three necked flask equipped with a distillation column, mechanical stirrer and nitrogen inlet at 120° C. under reduced pressure. After the distillation was complete the purified diol (144 lb), has an APHA color value of 3. Heating the thus purified 1,3-propanediol to reflux, under nitrogen for 3 hours caused the APHA color value to increase from 3 to 12. As described in Example 2, poly(1,3-propanediol) was made with the purified diol and the APHA color value of the polymer was 30.

What is claimed is:

1. A process for the purification of 1,3-propanediol comprising the steps of
   a) contacting 1,3-propanediol with an acid catalyst at a temperature above that required for impurities to react and below that required for extensive ether formation, said temperature being above about 100° C.; and
   b) isolating purified 1,3-propanediol from impurities, reacted impurities and the acid catalyst.

2. The process of claim 1 wherein the purified 1,3-propanediol is isolated by 1) separating the acid catalyst and 2) distilling 1,3-propanediol from the impurities and reacted impurities.

3. The process of claim 1 wherein the temperature in step a is less than 160° C.

4. The process of claim 3 wherein the temperature in step a is between 130 and 150° C.

5. The process of claim 1 wherein the acid catalyst is insoluble in 1,3-propanediol acid.

6. The process of claim 5 wherein the acid catalyst is a solid.

7. The process of claim 6 wherein the solid acid catalyst is selected from the group consisting of perfluorinated ion-exchange polymers (PFIEP) containing pendant sulfonic acid groups or pendant carboxylic acid groups, acid zeolites, and acid clays.

8. The process of claim 7 wherein the solid acid catalyst is selected from the group consisting of perfluorinated ion-exchange polymers containing pendant sulfonic acid groups, silica or alumina supported perfluorinated ion-exchange polymers containing pendant sulfonic acid groups and porous nanocomposites of perfluorinated ion-exchange polymers containing pendant sulfonic acid groups and silica.

9. The process of claim 1, wherein the temperature is at least 130° C.

10. A process for the purification of 1,3-propanediol consisting essentially of the sequential steps of:
    a) treating 1,3-propanediol with solid acid catalyst at a temperature of above about 100 to 160° C.;
    b) removing the solid acid catalyst by filtering or decanting; and
    c) isolating purified 1,3-propanediol from impurities by distillation.

11. The process of claim 10 wherein step a) is carried out at 130–160° C.

12. The process of claim 10 wherein step a) is carried out at 130–150° C.

13. The process of claim 10 wherein the 1,3-propanediol is cooled to room temperature prior to step b).

14. The process of claim 10 wherein the distillation is carried out under reduced pressure.

15. The process of claim 10 wherein the 1,3-propanediol contains colored precursors as an impurity and the colored precursors are transformed to separable compounds.

16. The process of claim 10 which is carried out in a continuous process.

17. The process of claim 10 which is carried out in a batch process.

18. A process for the purification of 1,3-propanediol comprising:
    a) treating a mixture consisting essentially of 1,3-propanediol and acid catalyst at a temperature of about 100–160° C.; and
    b) isolating purified 1,3-propanediol by distillation.

19. The process of claim 18 wherein step a) is carried out at 130–160° C.

20. The process of claim 18 wherein step a) is carried out at 130–150° C.

21. The process of claim 18 wherein the acid catalyst is a solid acid catalyst.

22. The process of claim 20 wherein the acid catalyst is a solid acid catalyst.

23. The process of claim 18 wherein treatment is carried out for 0.1–3 hours.

24. The process of claim 1, further comprising polymerizing the purified 1,3-propanediol in the presence of acid catalyst to obtain polyether polyol.

25. The process of claim 1, further comprising preparing a polyester from the purified 1,3-propanediol.

26. The process of claim 1, comprising first preparing 1,3-propanediol and then the steps a) and b).

* * * * *

UNITED STATES PATENT AND TRADEMARK OFFICE
CERTIFICATE OF CORRECTION

PATENT NO.    : 6,235,948 B1
DATED         : May 22, 2001
INVENTOR(S)   : Hari Babu Sunkara et al.

It is certified that error appears in the above-identified patent and that said Letters Patent is hereby corrected as shown below:

Column 1,
Line 14, replace "bomopolymers" with -- homopolymers --.

Column 5,
Line 34, replace "1,3-propanediol acid" with -- the 1,3-propanediol --.

Signed and Sealed this

Twenty-ninth Day of October, 2002

Attest:

JAMES E. ROGAN
Attesting Officer          Director of the United States Patent and Trademark Office